(12) United States Patent
Cozzolino et al.

(10) Patent No.: US 11,780,971 B2
(45) Date of Patent: Oct. 10, 2023

(54) ACTIVE YARNS AND TEXTILES FOR THE STABILIZATION AND CONTROLLED RELEASE OF ACTIVE COMPOUNDS

(71) Applicants: MATERIAS S.r.l., Naples (IT); NANO ACTIVE FILM S.r.l., Avellino (IT)

(72) Inventors: Antonietta Cozzolino, Nola (IT); Christophe Daniel, Fisciano (IT); Gaetano Guerra, Salerno (IT); Paola Rizzo, Naples (IT); Luigi Nicolais, Ercolano (IT)

(73) Assignees: MATERIAS S.r.l., Naples (IT); NANO ACTIVE FILM S.r.l., Avellino (IT)

( * ) Notice: Subject to any disclaimer, the term of this patent is extended or adjusted under 35 U.S.C. 154(b) by 175 days.

(21) Appl. No.: 17/264,652

(22) PCT Filed: Jul. 31, 2019

(86) PCT No.: PCT/IB2019/056530
§ 371 (c)(1),
(2) Date: Jan. 29, 2021

(87) PCT Pub. No.: WO2020/026164
PCT Pub. Date: Feb. 6, 2020

(65) Prior Publication Data
US 2021/0324151 A1 Oct. 21, 2021

(30) Foreign Application Priority Data
Jul. 31, 2018 (IT) .................. 102018000007712

(51) Int. Cl.
*C08J 3/20* (2006.01)
*A61K 8/81* (2006.01)
(Continued)

(52) U.S. Cl.
CPC .............. *C08J 3/203* (2013.01); *A01N 25/34* (2013.01); *A01N 31/08* (2013.01); *A01N 31/16* (2013.01);
(Continued)

(58) Field of Classification Search
CPC .......... C08J 3/203; D01F 6/22; A61K 8/0208; A61K 8/33; A61K 8/347; A61K 8/8117;
(Continued)

(56) References Cited

U.S. PATENT DOCUMENTS 5,079,075 A * 1/1992 Yamasaki ................ D01F 6/22
442/329
2010/0167036 A1 7/2010 Buono et al.
2013/0280534 A1* 10/2013 Albunia ................ C08J 7/0427
521/64

FOREIGN PATENT DOCUMENTS

WO WO 2007/107897 A1 9/2007
WO WO 2012/089805 A1 7/2012

OTHER PUBLICATIONS

Albunia, A.R. et al., "Syndiotactic Polystyrene Films with a Cocrystalline Phase Including Carvacrol Guest Molecules," Journal of Polymer Science, 2014, vol. 52, 657-665.
(Continued)

*Primary Examiner* — Jianfeng Song
(74) *Attorney, Agent, or Firm* — Oblon, McClelland, Maier & Neustadt, L.L.P.

(57) ABSTRACT

The present invention regards yarns comprising at least 1% by weight of fibre of a syndiotactic polystyrene containing a co-crystalline phase comprising at least one active guest compound, textiles comprising the aforementioned yarns and methods for preparing the same.

13 Claims, 7 Drawing Sheets

(51) Int. Cl.
| | |
|---|---|
| A61K 8/02 | (2006.01) |
| A01N 25/34 | (2006.01) |
| A61K 47/32 | (2006.01) |
| A61K 8/33 | (2006.01) |
| A61K 8/34 | (2006.01) |
| A61K 31/05 | (2006.01) |
| A61K 31/11 | (2006.01) |
| A61K 31/085 | (2006.01) |
| A61K 31/16 | (2006.01) |
| A01N 31/16 | (2006.01) |
| A01N 35/02 | (2006.01) |
| A01N 31/08 | (2006.01) |
| C08F 12/08 | (2006.01) |
| D06M 13/00 | (2006.01) |
| D06M 16/00 | (2006.01) |
| D01F 6/22 | (2006.01) |

(52) U.S. Cl.
CPC ............ *A01N 35/02* (2013.01); *A61K 8/0208* (2013.01); *A61K 8/33* (2013.01); *A61K 8/347* (2013.01); *A61K 8/8117* (2013.01); *A61K 31/05* (2013.01); *A61K 31/085* (2013.01); *A61K 31/11* (2013.01); *A61K 47/32* (2013.01); *C08F 12/08* (2013.01); *D01F 6/22* (2013.01); *D06M 13/005* (2013.01); *D06M 16/00* (2013.01)

(58) Field of Classification Search
CPC ...... A61K 31/05; A61K 31/085; A61K 31/11; A61K 47/32; A01N 25/34; A01N 31/08; A01N 31/16; A01N 35/02; C08F 12/08; D06M 13/005; D06M 16/00
See application file for complete search history.

(56) References Cited

OTHER PUBLICATIONS

International Search Report and Written Opinion dated Nov. 15, 2019 in PCT/IB2019/056530 filed on Jul. 31, 2019.

\* cited by examiner

ACTIVE YARNS AND TEXTILES FOR THE STABILIZATION AND CONTROLLED RELEASE OF ACTIVE COMPOUNDS

FIELD OF THE INVENTION

The invention falls within the technical/scientific fields of industrial chemistry and engineering, more in particular within the field of yarns and functionalised technical textiles, capable of releasing active molecules, in particular molecules with anti-microbial activity.

STATE OF THE ART

Over the recent years, in the textile industry there has been a lot of attention around the creation of yarns and innovative textiles, which have—in their composition—molecules that confer particular advantageous properties.

These textiles can contain active compounds which improve the aesthetic properties or performance thereof and they are used in various industries, for example the cosmetics industry, the sports and military clothing industry and in the defense against environmental risks.

However, most research activities in this industry focus on the development of textiles with anti-microbial activities. As a matter of fact, the need to preserve the textiles against microbial contamination is highly felt by consumers and by operators of specific technical sectors.

Due to the high surface area and capacity to retain moisture, the textiles actually constitute a fertile ground for the growth of microorganisms, such as bacteria and fungi. The growth of the microorganisms leads to risks for the health of the user, in that it facilitates the development and spread of infections, and several unwanted effects on the textiles, for example generation of unpleasant odour, reduction of mechanical resistance and formation of stains.

The microbial contamination of textiles is particularly challenging in hospitals where it was observed that textiles are capable of transferring nosocomial infections from one patient to the other, but it is also challenging in other industries such as for example the sports clothing industry, furnishing materials industry, water purification filter industry and food industry.

Various techniques for conferring various properties to the textiles including anti-microbial activity, by using active compounds have been developed over the last years. Such techniques vary depending on the properties intended to be obtained, on the characteristics of the textile and specific type of compound used. In particular, there are two main approaches towards manufacturing functionalised textiles, depending on the way in which the action of the active molecules is performed. According to a first approach, the active compound, for example the anti-microbial agent, is embedded in the structure of the textile which serves as a reserve of the same and releases it slowly through a controlled release mechanism. In this type of functionalised textile, the compound carries out its action both on the surface of the fibre of the textile and in the surrounding environment.

Some methods that produce this type of textiles are for example based on embedding of active substances in chemical fibres, during melt-spinning process. For example, triclosan molecules (2,4,4-hydrophenyl trichloro (II) ether) or silver particles or particles of other metals can be added with the aim of obtaining an anti-microbial activity.

Other methods are instead based on the treatment of textile fibre in finishing processes, in which the active substance is embedded in the finishing polymer formulation.

The functionalised textiles obtained using these techniques reveal the drawback lying in the fact that the active compound in the textile reduces overtime, especially following washing processes, and thus the action thereof is carried out over a limited period of time. Furthermore, the active compound reserve cannot be easily restored.

A second category of textiles is characterised by the formation of a chemical bond between the textile fibres and the active compound. In this type of textiles, the active compound remains on the surface of the textile and it is not released into the surrounding environment. Thus, this type of functionalisation is used in case one does intend to obtain an action exclusively at the textile level. For example, in the case of molecules with anti-microbial activity, an exclusively biostatic action on the textile which protects it from bacterial or fungal contamination is obtained.

The methods for manufacturing these textiles are based on the modification of fibres through chemical reactions that make them reactive against active molecules to be bonded to the textile, preferably grafting reactions in which chains containing active functional groups are grafted on the basic polymer chains of the fibre. Such methods have the advantage of an active molecule activity that is generally stable upon washing the textile. However, they reveal the drawback of the grafting procedure significantly depending on the chemical nature of the basic fibre and thus they cannot be used on all materials.

A further limitation to the preparation of the functionalised textiles obtained using all the conventional methods described above lies in the fact that the latter leads to satisfactory results only upon using active molecules with a high stability, in particular against oxidation and which thus maintain the features thereof unaltered over time. In the case of anti-microbial agents, for example, this limits the use thereof in some molecules of natural origin, such as for example hexanal, which have the compatibility and tolerability characteristics that would make them optimal for this use but which deteriorate easily upon exposure to atmospheric oxygen.

Particularly felt is the need to provide new techniques for preparing functionalised textiles using active compounds, applicable to anti-microbial compounds but also to molecules having a different activity, which allow to restore—in the textile—the amounts of active compounds and thus the properties conferred by the latter, once the latter reduce and are lost following release over time and due to the washing operations, and so that they can also allow the use of easily oxidizable molecules.

Syndiotactic polystyrene (hereinafter indicated with s-PS too) is a thermoplastic polymeric material with an extremely complex polymorphism and it has five different crystalline forms and various scattered crystalline forms (mesomorphs). It is known that such polymer, starting from delta or epsilon nanoporous crystalline forms, is capable of forming co-crystalline phases for absorbing appropriate guest molecules, in which the polymer is present in form of type s(2/1)2 helices, which form low molecular mass guest molecules. A summary work describing these co-crystalline forms of s-PS is for example Guerra et al. Journal of Polymer Science, Part B: Polymer Physics (2012) 50, 305-322.

In such context, it was also proven that syndiotactic polystyrene films, in which the crystalline phase is a co-crystalline form with active molecules, for example carvacrol, are capable of slowly releasing the low molecular mass compound. (Albunia et al. J. Polym. Sci. Part B: Polym. Phys. (2014) 52, 657-665).

SUMMARY OF THE INVENTION

The present inventors obtained yarns and functionalised textiles containing syndiotactic polystyrene characterised by a co-crystalline phase with low molecular mass active guest compounds. Such products controllably release into the environment active molecules, which can be restored in a simple and quick manner. Furthermore, they are capable of chemically stabilising unstable molecules.

A first object of the present invention is a yarn, suitable for preparing textiles comprising at least 1% by weight of fibres of a syndiotactic polystyrene, the latter containing a co-crystalline phase comprising at least one active guest compound and characterised by a X-ray diffraction (CuKα) pattern comprising peaks having maxima at about 2θ: between 9.5° and 9.8°, between 16.3° and 16.6°, between 19.7° and 20°.

A second object of the present invention is a textile comprising a yarn according to the first object of the invention and wherein said syndiotactic polystyrene fibres, containing a co-crystalline phase comprising at least one active guest compound and characterised by a X-ray diffraction (CuKα) pattern comprising peaks having maxima at about 2θ: between 9.5° and 9.8°, between 16.3° and 16.6°, between 19.7° and 20°, constitute at least 1% by weight of the textile.

A third object of the present invention is a method for obtaining a yarn according to the first object of the invention.

A fourth object of the present invention is a method for producing a textile according to the second object of the invention.

A fifth object of the invention is a syndiotactic polystyrene containing a co-crystalline phase comprising at least one active guest compound and characterised by a X-ray diffraction (CuKα) pattern comprising peaks having maxima at about 2θ: between 9.5° and 9.8°, between 16.3° and 16.6°, between 19.7° and 20°, wherein said active compound is an unstable compound, for example susceptible to oxidation.

A sixth object of the invention is a method for restoring the amount of active compound in a yarn according to the first object of the invention or in a textile according to the second object of the invention, wherein said yarn or textile are immerged in a liquid composition, aqueous or alcoholic comprising said active compound at a concentration comprised between 0.1% and 40% by weight for a period of time that varies between 30 seconds and 24 hours.

DESCRIPTION OF THE FIGURES

FIG. 3 shows the desorption kinetics in air of hexanal from the activated flock obtained as described in example 3a.

FIG. 13 is a photographic image showing a cone yarn (panel A) and a textile (panel B) containing 4% of syndiotactic polystyrene activated with eugenol and 96% of cotton, obtained as described in Example 4a.

DEFINITIONS

Figure 1:
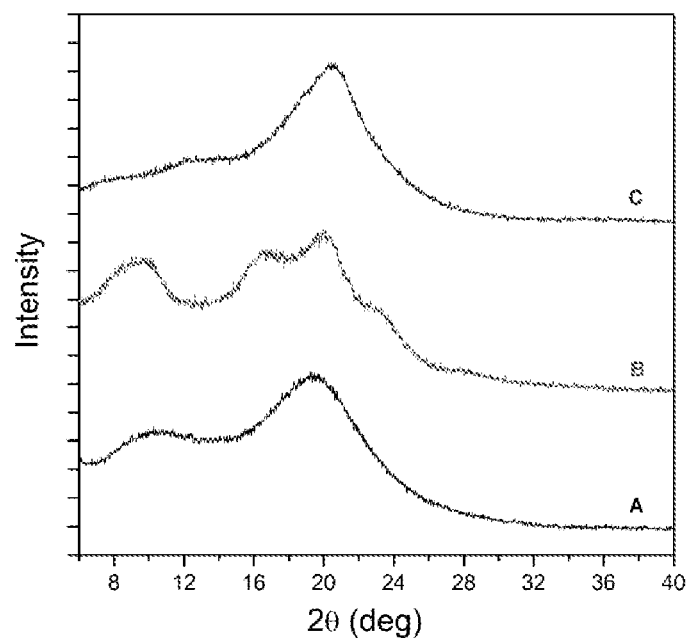
FIG. 1 shows X-ray diffraction spectrum (CuKα) of: amorphous syndiotactic polystyrene flock obtained as described in Example 1 b (curve A); amorphous syndiotactic polystyrene flock of Example 1, activated using hexanal in a 10% by weight methyl-acetate solution, as described in Example 3a (curve B) and mesomorphous syndiotactic polystyrene flock obtained as described in Example 2, after immerging in pure hexanal for 60 min, regarding which crystallisation is not observed and oxidation of hexanal to hexanoic acid is observed (curve C).

The expression "syndiotactic polystyrene" is used to indicate a polymer obtained from the polymerisation of styrene having a syndiotactic structure for at least long sequences of the chain, with length greater than ten monomer units. The expression includes both homopolymer and copolymers of styrene, containing at least 60% of styrene, with formula $CH_2=CH-R$ olefin, wherein R is an alkyl-aryl or a substituted aryl, containing between 6 and 20 carbon atoms or with other copolymerisable ethylene monomers. A particularly preferred copolymer is the styrene/paramethyl styrene copolymer.

The expression "yarn" is used to describe a yarn for use in the textile industry, obtained from a spinning method, consisting of an assembly of fibres held together by a torsion to form a long, continuous and flexible body (filament) and suitable to be interwoven for production of textiles. The torsion can be to the right or to the left.

The expression "spinning" is used to indicate a process that allows to obtain a yarn starting from fibres, comprising a fibre torsion step. The aforementioned fibres may be as flock or as continuous filament.

The expression "textile" is used to indicate an product with flat, thin and flexible surface consisting of a interweaving of filaments of yarns and obtained by weaving.

The expression "weaving" is used to indicate a process that allows to obtain a textile starting from two assemblies of yarn filaments (weft filaments and warp filaments) by weaving them according to different, specific shapes based on which textiles having various different structure are obtained.

The expression "average molecular weight" is used to indicate the average of the molecular weight of the polymeric chains forming the polymer.

The expression "amorphous" referring to syndiotactic polystyrene is used to indicate a syndiotactic polystyrene whose X-ray diffraction patterns do not have any diffraction peak but of the widened haloes only.

The expression "co-crystalline phase" is used to indicate a phase in which polymeric chains with orderly conformation host low molecular mass compounds referred to a "guest compounds" in the present document, in specific crystallographic positions.

The expression "compound" is used to indicate an organic or inorganic molecule, preferably an organic molecule, having a molecular weight below 900 daltons.

The expression "active compound" is used to indicate a compound capable of conferring, when embedded in a textile, a specific property thereto. For example, such expression includes molecules having anti-microbial activity.

The expression "degree of crystallinity" is used to indicate the percentage by weight of the sample consisting of crystalline phase.

The expression "molecular volume" is used to indicate the $M/(\rho N_a)$ ratio wherein M and $\rho$ are the molecular mass and the density, respectively and $N_a$ is Avogadro number.

The expression "X-ray diffraction (CuKα) pattern" according to the present invention refers to diffraction patterns collected using an automatic powder diffractometer, which uses the Kα radiation emitted by copper cathodes (Cu), for example a Brucker D8 automatic powder diffractometer, which uses the Kα radiation emitted by copper cathodes (Cu).

The expression "about", referring to the diffraction angle values 2θ, corresponding to peaks observed in X-ray diffraction patterns, is used to indicate that such value could vary up to a maximum of ±0.5° and preferably up to a maximum ±0.3°.

The expression "natural textile fibres" is used to indicate fibres of plant or animal origin. These for example include cotton, hemp, flax, wool and silk fibres.

The expression "chemical fibres" or "synthetic fibres" are used to indicate fibres obtained from polymers produced by man through polymerisation reactions. These for example include polyester, polyethylene, polyamide fibres.

The expression "artificial fibres" is used to indicate fibres obtained by transforming raw materials of natural origin. These for example include viscose fibres or rayon.

The expression "liquid" is used to indicate a pure compound in liquid state or a solution or even an emulsion in water of a compound.

The expression "biostatic activity" is used to indicate the control of growth and spread of microorganisms through a bacteriostatic and/or fungistatic activity.

The expression "biocide activity" is used to indicate the reduction, elimination, inactivation of microorganisms through a bactericidal and/or fungicidal activity.

The expression "unstable compound" is used to indicate a compound that tends to simultaneously react and transform under normal environmental conditions. For example, the expression includes compounds that react with air oxygen, with water, with acid compounds, undergoing oxidation, decomposition, polymerisation or combustion reactions.

The expression "compound susceptible to oxidation in air" is used to indicate a compound having productivity under oxidation by the molecular oxygen at ambient temperature calculated as the total of oxidised compound per liquid phase volume in presence of 0.2 bars of oxygen higher than 1 mM $L^{-1}$ $h^{-1}$, preferably higher than 10 mM $L^{-1}$ $h^{-1}$, measured as described in Vanoye t al, RSC Adv 2013, 3, 18931-18937.

DETAILED DESCRIPTION OF THE INVENTION

A first object of the present invention is a yarn, suitable for preparing textiles comprising at least 1% by weight of fibres of a syndiotactic polystyrene, the latter containing a co-crystalline phase comprising at least one active guest compound and characterised by a X-ray diffraction (CuKα) pattern comprising peaks having maxima at about 2θ: between 9.5° and 9.8°, between 16.3° and 16.6°, between 19.7° and 20°.

The aforementioned peaks are detected through an automatic powder diffractometer, which uses Kα radiation emitted by copper cathodes (Cu).

Preferably, the aforementioned syndiotactic polystyrene has a weighted average molecular mass greater than 100000 and a rrr syndiotactic triad content, as determined by $^{13}C$ NMR spectra, greater than 80%.

The aforementioned syndiotactic polystyrene has a degree of crystallinity, determined by measuring density using the floatation method, preferably at least 5%, more preferably at least 10%, even more preferably at least 20%, even more preferably at least 30%. According to a particularly preferred embodiment, the aforementioned syndiotactic polystyrene has a degree of crystallinity comprised between 20 and 60%, more preferably between 30 and 50%. The measurement of density using the floatation method is a technique well known to those skilled in the art and it is described in the book "*Polymer synthesis theory and practice: Fundamentals, Methods, Experiments*" by Braun et al., in sections 2.3.6 and 2.3.7.

The aforementioned active compound may be any compound capable of conferring the desired characteristics to the yarn.

The compound is preferably selected from among molecules which have anti-microbial, pharmacological, cosmetic activity and capable of conferring the aesthetics and pleasantness characteristics to the textile, such as perfuming for example.

The active compound has preferably a molecular volume lower than 0.4 $nm^3$. More preferably, the active compound also has an acid dissociation constant pKa>8, basic dissociation constant pKb>8, relative dielectric constant <20 and absence of solvent capacity with respect to syndiotactic polystyrene at a temperature below 100° C.

Preferred compounds having pharmacological activity according to the present invention are acetylsalicylic acid, isoniazid, methazolamide, metronidazole, sulfacetamide.

Preferred compounds having cosmetic activity according to the present invention are butyl hydroxyanisole and capric acid.

Preferred compounds capable of conferring perfume to the textile according to the present invention are butyl acetate, diacetyl, diallyl disulfide, ethyl acetate, guaiacol and linalool.

Preferably, the active compound has anti-microbial activity. Said anti-microbial activity can be a biostatic or biocide activity. Preferred compounds having anti-microbial activity according to the present invention are anethole, camphor, carvacrol, carvone, coumarin, eugenol, hexanal, tyrosol, geraniol, isoprenol, limonene, menthol, myrcene, caffeic acid, cinnamic acid, catechol, pyrogallol and thymol.

According to a particularly preferred embodiment, the active compound is selected from among carvacrol, hexanal, eugenol, thymol and tyrosol.

The active compound is contained in the syndiotactic polymer at an amount preferably greater than 1% by weight, more preferably greater than 5% by weight, even more preferably greater than 10%, even more preferably greater than 20% by weight, with respect to the total weight of the polymer. Preferably, the active compound is contained in the syndiotactic polymer at an amount comprised between 5 and 50% more preferably between 10 and 30%.

Figure 5:
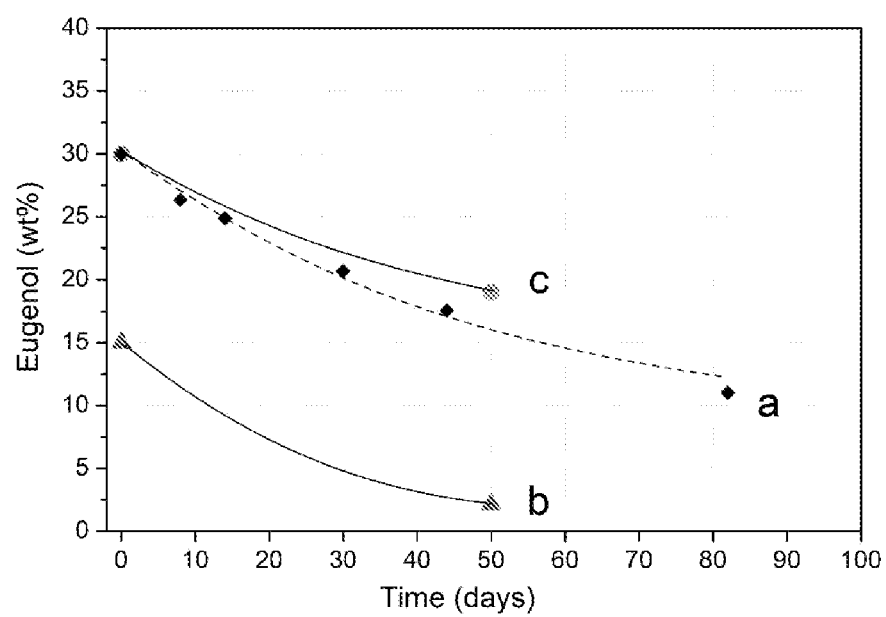
FIG. 5 shows the desorption kinetics in air of eugenol from the flocks activated by immersion in pure eugenol (curve a) as described in example 3c, or eugenol in aqueous solution at 0.25% (curve b) or 0.6% (curve c) as described in Example 3d.

As demonstrated in the experimental part, in FIG. 5 and in examples 3c and 3d, the syndiotactic polystyrene fibres according to the invention have a high active compounds absorption capacity, much higher with respect to what is observed relating to the compounds with amorphous syndiotactic polystyrene fibres or containing non-porous crystalline phases.

The yarn according to the first object of the invention can solely consist of fibres of said syndiotactic polystyrene as defined above or, alternatively, fibres of said syndiotactic polystyrene and one or more of the natural and/or synthetic textile fibres.

The yarn according to the invention comprises fibres of said syndiotactic polystyrene at an amount comprised between 1 and 100% by weight, preferably between 5 and 100% by weight, even more preferably between 20 and 100% by weight, with respect to the total weight of the yarn.

The yarn according to the invention comprises natural and/or synthetic textile fibres at an amount comprised between 0 and 99% by weight, preferably between 0 and 95% by weight, even more preferably between 0 and 80% by weight, with respect to the total weight of the yarn.

In particular, according to a first preferred embodiment, the fibres of the yarn according to the invention consist in fibres of a syndiotactic polystyrene as defined above, containing a co-crystalline phase comprising at least one active guest compound and characterised by an X-ray diffraction (CuKα) pattern comprising peaks having maxima at about 2θ: between 9.5° and 9.8°, between 16.3° and 16.6°, between 19.7° and 20°, and one or more natural and/or synthetic textile fibres. The yarn according to this embodiment of the invention comprises fibres of said syndiotactic polystyrene at an amount comprised between 1 and 99% by weight, preferably between 5 and 99% by weight, even more preferably between 20 and 99% by weight, even more preferably between 50 and 99% by weight, with respect to the total weight of the yarn and natural and/or synthetic textile fibres at an amount comprised between 1 and 99% by weight, preferably between 1 and 95% by weight, even more preferably between 1 and 80% by weight, even more preferably between 1 and 50% by weight, with respect to the total weight of the yarn.

According to an alternative preferred embodiment, the fibres of the yarn according to the invention consist of 100% of fibres of a syndiotactic polystyrene as defined above, containing a co-crystalline phase comprising at least one active guest compound and characterised by an X-ray diffraction (CuKα) pattern comprising peaks having maxima at about 2θ: between 9.5° and 9.8°, between 16.3° and 16.6°, between 19.7° and 20°.

A second object of the present invention is a textile comprising a yarn according to the first object of the invention and wherein said syndiotactic polystyrene fibres, containing a co-crystalline phase comprising at least one active guest compound and characterised by a X-ray diffraction (CuKα) pattern comprising peaks having maxima at about 2θ: between 9.5° and 9.8°, between 16.3° and 16.6°, between 19.7° and 20°, consist of at least 1% by weight, with respect to the total weight of the textile. According to a particularly preferred embodiment, the textile according to the invention is obtained by weaving solely yarns according to the first object of the invention.

According to an alternative embodiment, the textile according to the invention is obtained by weaving yarns according to the first object of the invention and different yarns.

In such case, the yarn according to the invention is present in the textile at an amount of at least 1% by weight, preferably greater than 10% by weight and even more preferably greater than 90% by weight.

Furthermore, in such case said syndiotactic polystyrene fibres constitute at least 1% by weight, preferably at least 4% by weight, even more preferably at least 10% by weight, with respect to the total weight of the textile.

The amount of the aforementioned syndiotactic polystyrene in the textile depends on the functionalisation purpose of the textile and on the amount of active guest compound required to obtain the desired technical effect.

In the textile according to the present invention, the active guest compound may exercise its action at textile level, for example protecting it against microbial contamination or conferring it a particular perfume, and/or in the surrounding environment by releasing it at controlled speed. In particular, as shown in the experimental part, preferably in the textiles according to the invention, the active compounds have a combined activity at textile level and at the surrounding environment level. As a matter of fact, as shown in Examples 3c to 3e, the syndiotactic polystyrene fibres according to the invention slowly release the active guest compounds, at a different speed when they are exposed to air with respect to an aqueous environment.

Thus, for example in the case of anti-microbial activity guest compounds, there is obtained the combination of a biostatic effect on the textiles and, in particular when the textile comes into contact with the liquids or humidity, a biostatic or biocide action on the environment, depending on whether it exceeds the Minimum Inhibitory Concentration (MIC) or the Minimum Bactericidal Concentration (MBC). This makes the textiles according to the invention containing anti-microbial activity compounds particularly suitable for use as textiles for hospital linen or for covering settees and armchairs used in spaces open to the public.

As described hereinafter, with respect to the textiles of the prior art, the textiles according to the present invention have the advantage lying in the fact that the amount of active guest compound—that is slowly released by the textile over time and thus reduces—can be restored, even during the washing process. As a matter of fact, as demonstrated in Example 3a, the persistence in the syndiotactic polymer with high degree of crystallinity, allows an easy regeneration of the yarn and textiles activity.

Furthermore, as discussed hereinafter, the textiles according to the present invention have the advantage of being functionalised also using guest molecules that could not be used with the textiles functionalisation techniques of the prior art due to the instability thereof, for example upon oxidation.

A third object of the present invention is a method for obtaining a yarn according to the first object of the invention.

According to a preferred embodiment such method comprises the following stages:

a) providing a fibre, preferably a flock or filament, of syndiotactic polystyrene in amorphous phase;

b) providing a liquid suitable to form a co-crystalline phase in the syndiotactic polystyrene and comprising an active compound having a molecular volume smaller than 0.4 nm$^3$ and immerging the fibre of stage a), in said liquid;

c) maintaining said fibre immerged in said liquid for a time sufficient to form a co-crystalline phase with the active compound contained therein;

d) removing the fibre from the liquid and drying in air;

e) performing a textile spinning of one or more fibres obtained in stage d) and, optionally, one or more natural and/or synthetic fibres to obtain a yarn.

Said amorphous syndiotactic polystyrene fibre can be obtained by means of any method for processing it that leads to amorphization. For example, methods for obtaining amorphous syndiotactic polystyrene were described in Guerra et al, Macromolecules, 1990, 23, 1539 and in WO2012089805.

Preferably, said amorphous syndiotactic polystyrene fibre is obtained by melt-spinning syndiotactic polystyrene, at temperatures exceeding 250° C. and lower than 300° C.

According to an alternative preferred embodiment, the yarn according to the first object of the invention can be obtained using a method that provides for the following stages:

a') providing a fibre, preferably a flock or filament, of syndiotactic polystyrene in amorphous phase;

b') performing a textile spinning of one or more fibres of stage a) and, optionally, one or more natural and/or synthetic fibres to obtain a yarn;

c') providing a liquid suitable to form a co-crystalline phase in the syndiotactic polystyrene and comprising an active compound having a molecular volume smaller than 0.4 nm$^3$ and immerging the yarn of stage b'), in said liquid;

d') maintaining said yarn immerged in said liquid for a time sufficient to form a co-crystalline phase with the active compound contained therein;

e') removing the yarn from the liquid and drying in air.

A fourth object of the present invention is a method for producing a textile according to the second object of the invention.

According to a particularly preferred embodiment, such method consists in weaving yarns according to the first object of the invention.

Preferably, said yarn is obtained through one of the aforementioned methods according to the third object of the invention.

The textile can be obtained using any of the conventional weaving techniques.

According to an alternative embodiment, the aforementioned method comprises the weaving a yarn comprising syndiotactic polystyrene fibres in amorphous phase and the subsequent obtainment of a co-crystalline phase with the active compound.

In particular, according to such embodiment, the method provides for the following stages:

a") obtaining a textile by weaving a yarn comprising a syndiotactic polystyrene fibres in amorphous phase;

b") providing a liquid suitable to form a co-crystalline phase in the syndiotactic polystyrene comprising an active compound having a molecular volume smaller than 0.4 nm$^3$ and immerging the textile obtained in stage a") in said liquid for a period sufficient to form a co-crystalline phase with the active compound;

c'") removing the textile from the liquid and drying in air.

In all the aforementioned methods for producing a yarn or textile according to the invention, the liquid suitable to form a co-crystalline phase in the syndiotactic polystyrene of stage b), c') or b"), respectively, is a liquid containing an active compound and/or a solvent suitable to form a co-crystalline phase in the syndiotactic polystyrene, in particular having the following characteristics: molecular volume lower than 0.4 nm$^3$, acid dissociation constant pKa>8, basic dissociation constant pKb>8, relative dielectric constant <20 and absence of solvent capacity with respect to syndiotactic polystyrene at temperatures below 100° C.

The aforementioned liquid, is selected from among said active compound in pure liquid form and solutions and emulsions of said active compound.

In particular, when said liquid of stage b), c') or b") consists in the active compound in pure liquid form, the compound has the aforementioned characteristics suitable to form a co-crystalline phase in syndiotactic polystyrene and, in particular, molecular volume lower than 0.4 nm$^3$, acid dissociation constant pKa>8, basic dissociation constant pKb>8, relative dielectric constant <20 and absence of solvent capacity with respect to syndiotactic polystyrene at temperatures below 100° C.

On the other hand, should said liquid of stage b), c') or b") consist in solutions or emulsions of said active compound, at least from among the active compound and the solvent of the solution or emulsion has characteristics suitable to form a co-crystalline phase in syndiotactic polystyrene. Such characteristics in particular consist in molecular volume lower than 0.4 nm³, acid dissociation constant pKa>8, basic dissociation constant pKb>8, relative dielectric constant <20 and absence of solvent capacity with respect to syndiotactic polystyrene at a temperature below 100° C.

Active compounds having the aforementioned characteristics suitable to form a co-crystalline phase in syndiotactic polystyrene and which can thus be used in the aforementioned liquid in presence of solvents that do not have such characteristics, are for example the anti-microbial compounds anethole, camphor, carvacrol, carvone, coumarin, eugenol, hexanal, geraniol, isoprenol, limonene, menthol, myrcene, catechol, pyrogallol, thymol and tyrosol, the perfume-conferring compounds butyl acetate, diacetyl, diallyl disulfide, ethyl acetate, guaiacol and linalool.

Active compounds having a molecular volume lower than 0.4 nm³ but do not have characteristics suitable to form a co-crystalline phase in syndiotactic polystyrene and thus must be used in the aforementioned liquid in combination with a solvent having such characteristics are the anti-microbial compounds caffeic acid, cinnamic acid, the compounds having pharmacological activity acetylsalicylic acid, isoniazid, methazolamide, metronidazole and sulfacetamide and the compounds having cosmetic activity butyl hydroxyanisole and capric acid.

The solvent is preferably environmental-friendly.

Preferred solvents according to the invention having the aforementioned characteristics suitable to form a co-crystalline phase in syndiotactic polystyrene, in particular molecular volume lower than 0.4 nm³, acid dissociation constant pKa>8, basic dissociation constant pKb>8, relative dielectric constant <20 and absence of solvent capacity with respect to syndiotactic polystyrene at a temperature below 100° C., are methyl acetate, ethyl acetate and methyl ethyl ketone.

Preferred solvents according to the invention that do not have characteristics suitable to form a co-crystalline phase in syndiotactic polystyrene but that can be used in the aforementioned liquid combined with an active compound having such characteristics are for example water and ethyl alcohol.

For example, an emulsion according to the invention consists of eugenol dispersed in water.

Preferably, solutions or emulsions of the active compound comprising a concentration of the active compound comprised between 0.1 and 100% and more preferably between 1% and 50%.

The aforementioned fibre of stage a), yarn of stage b') or textile obtained in stage a") are kept immersed in the aforementioned liquid of stage b), c') or b") for a period of time sufficient to obtain an end product with degree of crystallinity of at least 5%, preferably comprised between 5% and 50%. Such period of time depends on the nature of the active compound and the concentration thereof in the aforementioned immersion liquid.

Generally, such period of time varies between 30 seconds, when using the pure liquid form of the active compound, and 12 hours, when using a low concentration emulsion or solution of the active compound on the other hand, for example between 0.2 and 1% by weight.

The present inventors surprisingly observed that the formation of a co-crystalline phase of the active compound with syndiotactic polystyrene protects unstable active compounds against unwanted reactions. Without being bound to a specific mechanism, the present inventors found out that the formation of the co-crystalline phase slows the spread of reagent molecules towards active guest compounds and/or increases the energy for activating unwanted reactions, due to the confinement of the active compounds and the corresponding activated complexes in the crystalline cavity of the polymer.

The present inventors found out that active compounds having groups susceptible to oxidation, such as for example aldehydes, such as hexanal, are protected against oxidation reactions in the crystalline phase.

In particular, as described in Examples 3a and 3b, the co-crystallisation of hexanal with the polymer allows to keep the characteristics intact, while the embedding thereof in a mesomorph form of the polymer without forming the nanoporous crystalline phases leads to almost full oxidation of hexanal into hexanoic acid.

Thus, a fifth object of the invention is a syndiotactic polystyrene containing a co-crystalline phase comprising at least one active guest compound and characterised by a X-ray diffraction (CuKα) pattern comprising peaks having maxima at about 2θ: between 9.5° and 9.8°, between 16.3° and 16.6°, between 19.7° and 20°, wherein said active guest compound is an unstable compound, preferably a compound susceptible to oxidation in air.

Organic compounds having the aforementioned characteristics that can be advantageously stabilised through the formation of the co-crystalline phase using the syndiotactic polymer for example are the aldehydes that are oxidised in air in the corresponding carboxylic acids such as for example, hexanal and trans-2-hexanal.

The yarn or the textile according to the first and to the second object of the invention, wherein the active guest compound content is reduced over time, can be restored with the active compound, for example during washing, using an appropriate liquid composition. Such composition comprises said active compound at a concentration comprised between 0.1% and 40% by weight, in water or alcohol. Preferably, said liquid composition is an aqueous or alcoholic solution or emulsion of the active compound.

The active compound contained in the aforementioned liquid composition is the same present in the yarn or in the textile and it has characteristics suitable to form a co-crystalline phase in syndiotactic polystyrene, with molecular volume lower than 0.4 nm³, acid dissociation constant pKa>8, basic dissociation constant pKb>8, relative dielectric constant <20 and absence of solvent capacity with respect to syndiotactic polystyrene at temperatures below 100° C.

A sixth object of the present invention is a method for restoring the amount of active compound in a yarn according to the first object of the invention or in a textile according to the second object of the invention, wherein said yarn or textile are immersed in a composition according to the sixth object of the invention for a period that varies between 30 seconds and 24 hours, preferably between 2 minutes and 1 hour, even more preferably between 5 and 10 minutes in a liquid composition according to the sixth object of the invention.

The restoration of the amount of active compound in the aforementioned yarn or textile can be carried out during the operations of washing the same.

Thus, according to the seventh object of the invention, particularly preferred is a method for restoring the amount of active compound in a yarn according to first object of the invention or a textile according to the second object of the invention comprising:

a''') washing the yarn or textile using a cleaning composition;

b''') rinsing, comprising a final rinsing step using a liquid composition according to the sixth object of the invention for a period of time between 30 seconds and 24 hours, preferably between 2 minutes and 1 hour, even more preferably between 5 and 10 minutes.

Preferably, the cleaning composition of stage am) comprises surfactants selected from among those commonly used for washing textiles, for example sodium lauryl sulphate, lauryl ethoxy sulphate, benzalkonium chloride, dodecyl-betaine or lecithin.

Below are non-limiting examples describing the invention.

Example 1—Amorphous Syndiotactic Polystyrene Flock

Example 1a

Syndiotactic polystyrene manufactured by Dow Chemical and sold under the tradename Questra was used. The granule was subjected to a melt-spinning process on a laboratory spinning installation, at a temperature of 305° C., using spinnerets with holes measuring 0.70 mm in diameter, obtaining a flock with filaments measuring about 30 µm in diameter. The flock was amorphous, as shown in the X-ray diffraction (CuKα) pattern of FIG. 1, curve A. The X-ray diffraction pattern in this and in the subsequent examples was carried out by means of a Brucker D8 automatic powder diffractometer, which uses Kα radiation emitted by copper cathodes (Cu).

Example 1b

Syndiotactic polystyrene manufactured by Idemitsu Chemical Japan and sold under the tradename Xarec® 300ZC was used. The granule was subjected to a melt-spinning process on an industrial spinning installation, at a temperature of 310° C., using spinnerets with holes measuring 1.0 mm in diameter, obtaining a flock with filaments measuring about 20 µm in diameter. The flock was amorphous and it has an X-ray diffraction pattern similar to the one shown in FIG. 1, curve A.

Example 2—Mesomorphous s-PS Flock

Syndiotactic polystyrene manufactured by Idemitsu Chemical Japan and sold under the tradename Xarec® 90ZC was used. The flock obtained by melt spinning at 310° C., using spinnerets measuring 0.7 mm in diameter, the spinning process being followed by an ironing process, consists of filaments measuring about 20 µm in diameter, using a cooling and spinning speed that lead to a mesomorphous product. The flock is mesomorphous, as shown by the X-ray diffraction (CuKα) pattern of FIG. 1, curve C, and by the presence of the typical absorption peak in FTIR spectra regarding a vibrational mode of the zig-zag-planar pattern of syndiotactic polystyrene, located at 1222 cm$^{-1}$ in an area of the spectrum not shown in 2B.

Example 3—Preparation of Activated s-PS

Example 3a

The amorphous flock prepared in example 1a was immerged in an hexanal solution in methyl-acetate (AcOMe) at 10% by weight for 60 minutes and subsequently left in air for 3 days.

After treatment with the solution, the activated flock had the X-ray diffraction (CuKα) pattern indicated in FIG. 1, curve B. As shown in such figure, the X-ray diffraction (CuKα) pattern shows reflexions with intensity greater than 2θ about equal to 9.5°, 16.6°, 20.0°, indicating the presence of a co-crystalline phase, rather scattered.

Furthermore, the FTIR spectra, using the DRIFT technology, of the amorphous flock prepared in example 1a and of the corresponding flock activated with hexanal in 10% by weight methyl-acetate solution show peaks typical of the helix shape of syndiotactic polystyrene, such as for example the peak at 571 cm$^{-1}$ in an area of the spectrum not shown in 2A, clearly indicating that the absorption of the solution leads to the formation of helices typical of clathrate crystalline phases, starting from the amorph.

Figure 2A:
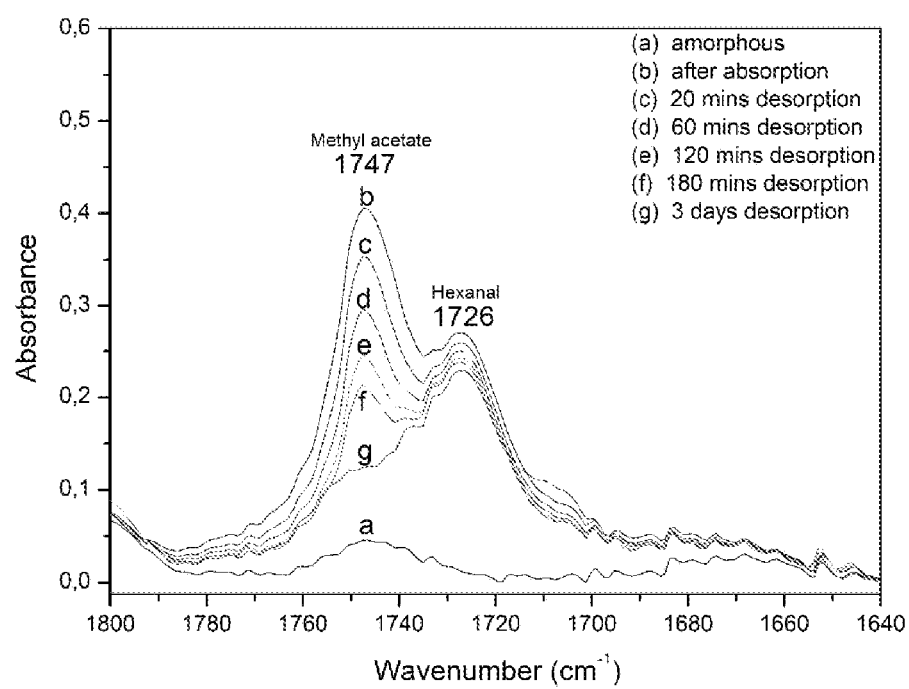
FIG. 2A shows FTIR spectra of the amorphous syndiotactic polystyrene flock obtained as described in Example 1a (curve a) and of the corresponding flock activated with hexanal in a 10% by weight methyl-acetate solution, after 60 minutes of immersion, followed by desorption in air for 20 (curve c), 60 (curve d), 120 (curve e) and 180 minutes (curve f) and 3 days (curve g), as described in Example 3a. The absorbance peak at 1747 $cm^{-1}$ corresponds to methyl acetate, while the absorbance peak at 1726 $cm^{-1}$ corresponds to hexanal.

The FTIR spectra also show the presence of absorption peaks typical of methyl acetate and hexanal. As observable in the FTIR spectrum indicated in FIG. 2A, the methyl acetate is desorbed spontaneously already at ambient temperature after 3 days (curve g), while after 3 days of desorption at ambient temperature hexanal is still present, without any oxidation under hexanoic acid, at an amount (analysed thermogravimetrically) equal to about 8% by weight of the polymer.

Thus, the obtained results show that the co-crystallisation in the nano-crystalline reticulum of syndiotactic polystyrene protects it against oxidation phenomena, increasing the stability thereof.

Spectral subtraction techniques allow to determine the degree of crystallinity of the crystalline form equal to 40%. Such degree of crystallinity is maintained even after desorption of hexanal in the long term. For example, after 3 days of desorption when about 20% of hexanal has been desorbed in the environment, the degree of crystallinity remains close to 40%.

Figure 3:
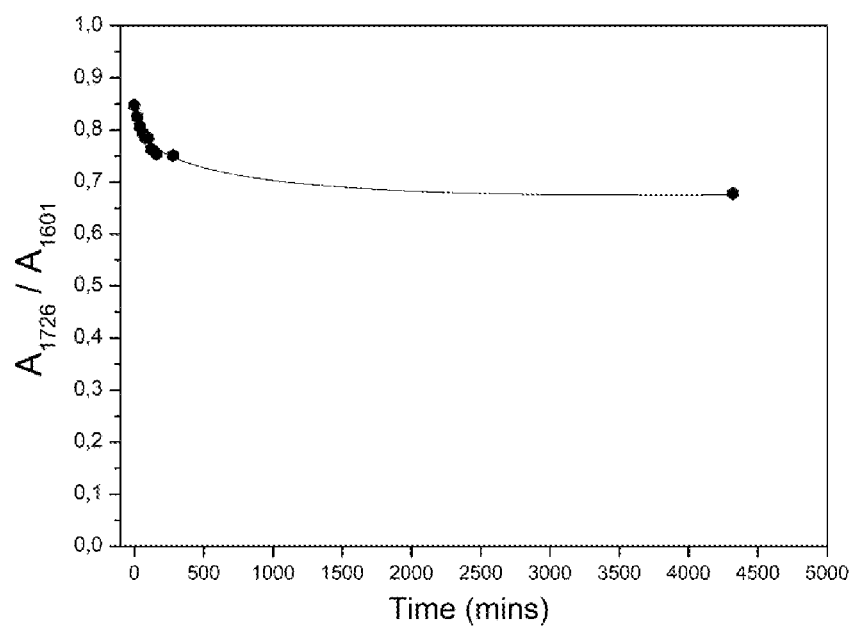

The measurements of intensity of the hexanal peak at 1726 cm$^{-1}$ with respect to the peak of host polymers, associated with the thermogravimetrically measurements, allowed to obtain the amount of hexanal embedded in the nano-crystalline reticulum of syndiotactic polystyrene and the desorption kinetics of hexanal shown in FIG. 3.

Example 3b

The mesomorphous flock prepared in example 2 was immerged in liquid hexanal for 60 minutes and subsequently left in air for 60 minutes.

Figure 2B:
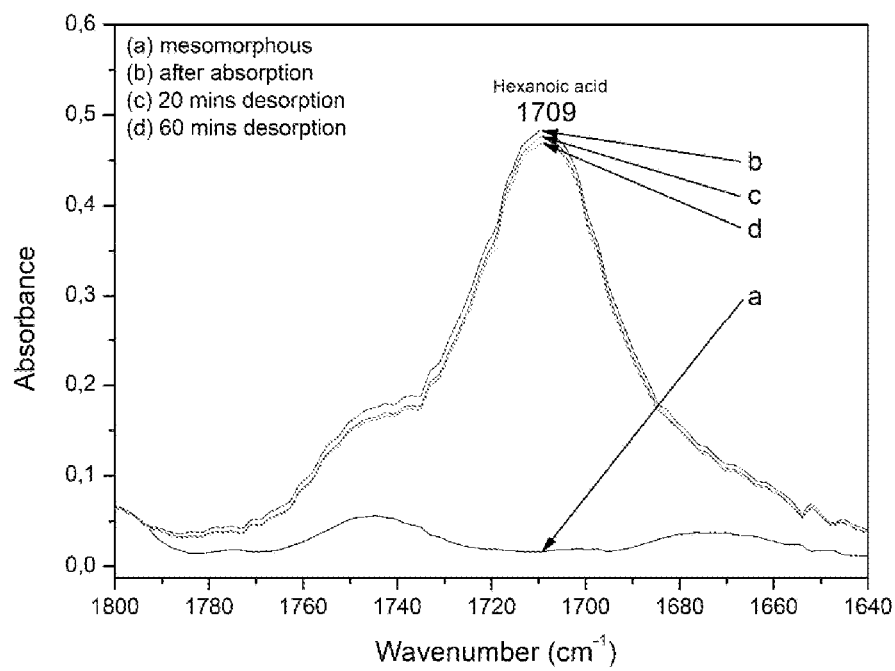
FIG. 2B shows FTIR spectra of the mesomorphous syndiotactic polystyrene flock obtained as described in example 2 (curve a) and of the corresponding immerged in pure hexanal for 60 minutes (curve b), followed by desorption in air for 20 (curve c) and 60 minutes (curve d), as described in Example 3b. The absorbance peak at 1709 $cm^{-1}$ corresponds to hexanoic acid.

FTIR spectra, using DRIFT tech, of the mesomorphous flock prepared in example 2 and of the flock activated with hexanal, prepared in example 3b, were compared in FIG. 2B. The absence of peaks typical of the helix shape of syndiotactic polystyrene, such as for example the peak at 571 cm$^{-1}$ (in an area of the spectrum not shown in FIG. 2B), clearly indicates that the absorption of the solution does not lead to the formation of crystalline phases.

Furthermore, the presence of absorption peaks typical of hexanoic acid and the absence of peaks of hexanal are clearly observable. Thus, the absorption in the mesomorphous polymer does not protect hexanal against oxidation by hexanoic acid.

Example 3c

The amorphous flock prepared in example 1a was immerged in liquid eugenol for 30 minutes and subsequently left in air for 8 days.

Figure 4:
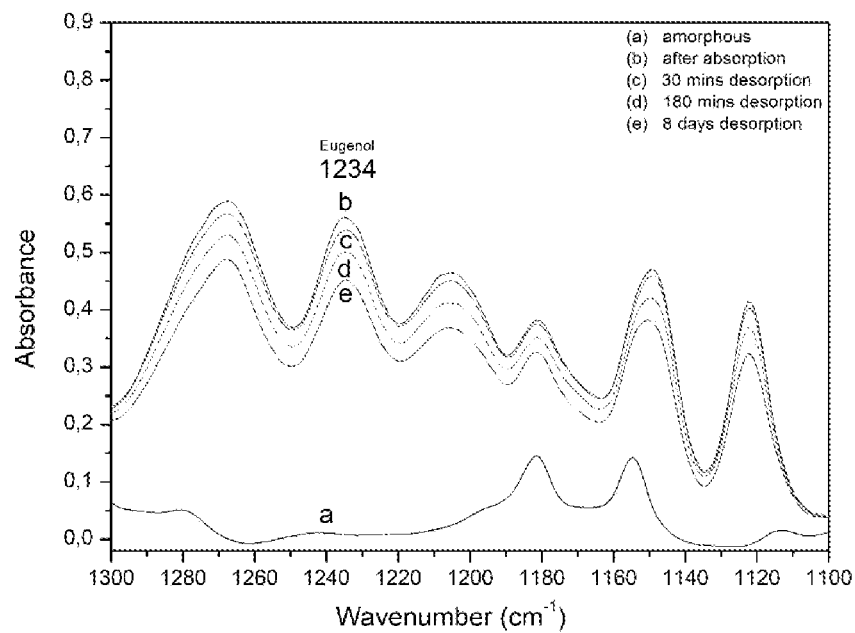
FIG. 4 shows the FTIR spectra of the amorphous syndiotactic polystyrene flock obtained as described in Example 1a (curve a) and of the corresponding activated with liquid eugenol for 30 seconds, as described in example 3c (curve b), followed by desorption in air for 30 (curve c), 180 minutes (curve d) and 8 days (curve e). The absorbance peak at 1234 $cm^{-1}$ corresponds to eugenol.

FTIR spectra, using DRIFT tech, of the amorphous flock prepared in example 1a and of the flock treated using liquid eugenol as described above were compared in FIG. 4. The presence of peaks typical of the helix shape of syndiotactic polystyrene, such as for example the peak at 571 cm$^{-1}$ (in an area of the spectrum not shown in FIG. 4), clearly indicates that the absorption of the solution leads to the formation of a syndiotactic polystyrene/eugenol crystalline phase.

A desorption kinetics of eugenol by the activated flock obtained as outlined above is indicated in FIG. 5, curve a. The amount of eugenol absorbed (analysed thermogravimetrically) is equal to 30%.

The release of eugenol in air at ambient temperature is limited. As a matter of fact, only 3% of the eugenol present is released after 24 h.

Figure 6:
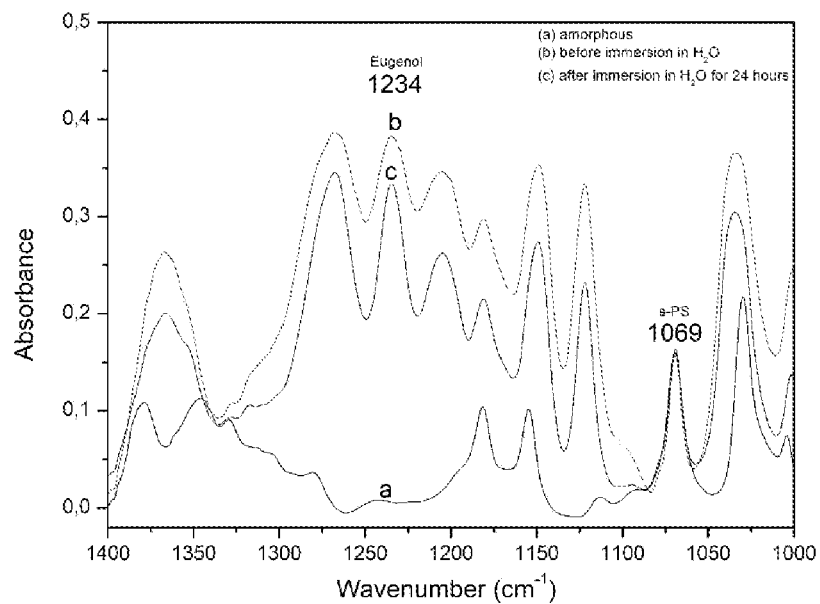
FIG. 6 shows the FTIR spectra of the amorphous syndiotactic polystyrene flock (curve a) and of the activated with liquid eugenol first (curve b) and after (curve c) immersion in water for 24 h, as described in Example 3c.

Furthermore, the release of eugenol in water by the activated flock obtained as outlined above was evaluated. The FTIR spectra (FIG. 6) show the release, by the flock activated with liquid eugenol, of about 20% of the absorbed eugenol after 24 h of immersion in water at ambient temperature. Thus, the data shows that eugenol is extracted faster from water, a potential microbial habitat.

Thus, the release kinetics of the anti-microbial guest molecule by the flock is extremely slow in the absence of water and it allows to obtain high biostatic activity textiles.

The anti-microbial molecule, on the other hand, is released more rapidly when the flock comes into contact with water and this allows to obtain textiles that also carry out a bioactive function in presence of water, a bacterial growth habitat.

Example 3d

The amorphous flock prepared in example 1 b was immerged for 12 hours in an aqueous emulsion with a eugenol content equal to 0.25% or 0.6% by weight, and then subsequently left in air. The obtained activated flock has a eugenol content equal to 15% and 30%, respectively. The corresponding desorption kinetics in air of the two samples is shown in FIG. 5 (curve b and curve c, respectively).

The X-ray diffraction patterns, of the flock activated with eugenol in water at 0.6% (FIG. 7 curve C), show the presence of diffraction peaks at about 2θ equal to 9.6°, 16.1°, 19.7°, indicating the formation of a co-crystalline phase.

Figure 7:
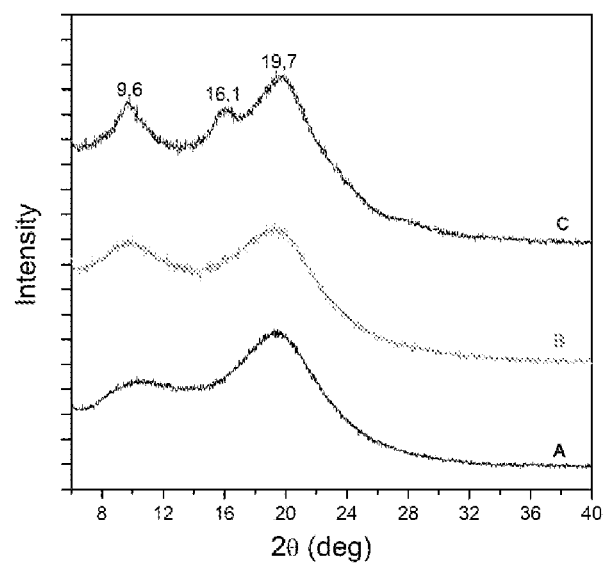
FIG. 7 shows the X-ray diffraction spectrum (CuKα) of the amorphous s-PS flock (curve A) and of the corresponding flocks activated with eugenol in aqueous solution 0.25% (curve B) and 0.6% (curve C) by weight, as described in Example 3d.

It is clear that the slower release of eugenol highlighted in FIG. 5, curve c) is due to the presence of such molecule as guest of the crystalline phase, as proven by the X-ray diffraction pattern of FIG. 7 curve C. At about six months from the activation process, the thermogravimetric analysis of the flock treated using eugenol in aqueous solution at 0.6% was conducted and it was observed that the flock had a eugenol concentration equal to 14% by weight. An anti-microbial assay regarding the *Staphylococcus aureus* strain was then conducted on the flock with the aim of verifying the antibacterial effectiveness thereof, using the UNI EN ISO 20743 method. In detail, the stock solution of the *Staphylococcus aureus* bacterial strain was prepared and grown on a PCA medium at 37° C. for 24 hours. A sterile loop was used to collect a bacterial colony and immerged in 20 ml of peptone water, the solution thus obtained was incubated at 37° C. for 24 hours under stirring. Dilutions were carried out up to achieving a solution with an estimated bacterial concentration of $10^5$-$10^6$ cells/mL. At this point, an aliquot equal to 0.2 mL of such solution was pipetted on 0.1 g samples of flock containing the anti-microbial agent, previously cut into small pieces, and it was then diluted using 20 mL of saline solution, the entirety was then incubated at 37° C. for 24 hours. An aliquot equal to 1 mL was collected from this bacterial solution and diluted by three orders, the last 1 mL aliquot was placed in a PCA medium which was then incubated at 37° C. for 24-48 hours. Such period of incubation was followed by a visual inspection of the media to verify the presence or absence of bacterial growth.

Figure 8:
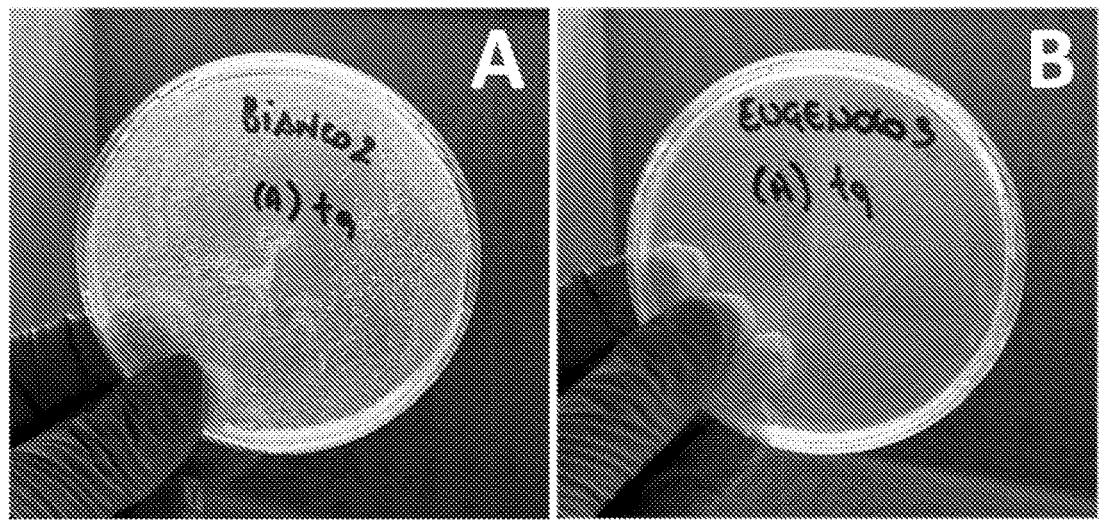
FIG. 8 is a photographic image showing the results of the anti-microbial assay, which shows the bacterial growth in a Petri dish containing medium treated with the flock obtained in Example 1 (panel A) or the flock activated with eugenol (panel B), as described in Example 3d.

As observable in the images of FIG. 8, in the Petri dishes treated with the activated flock no bacterial growth was observed. Thus, this experiment shows that the flock is capable of releasing eugenol in water at amounts suitable to obtain an antibacterial effect, i.e. so as to exceed the Minimum Inhibitory Concentration (MIC=0.625 mg/mL).

Example 3e

The amorphous flock prepared in example 1a was immerged in a methyl-acetate solution of thymol at 10% or at 30% by weight, for a period of 10 min, and subsequently left in air.

Figure 9:
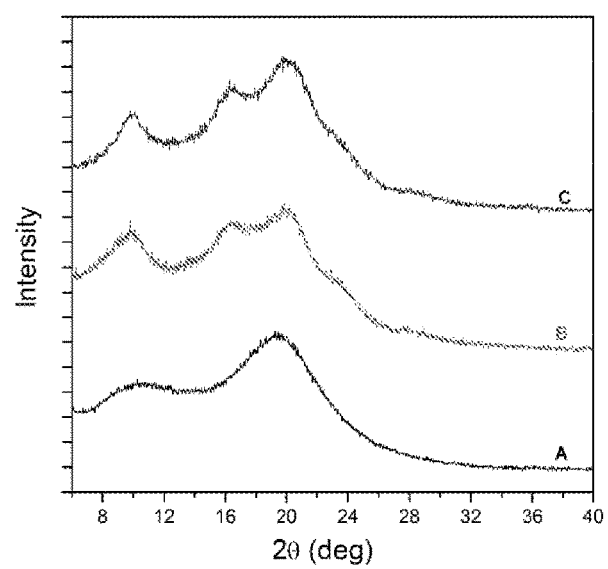
FIG. 9 shows the X-ray diffraction spectrum (CuKα) of the amorphous syndiotactic polystyrene flock obtained as described in example 1 (curve A) and of the corresponding flocks activated with thymol in a methyl acetate solution respectively at 10% (curve B) and 30% (curve C) by weight, obtained as described in example 3e.

The X-ray diffraction patterns of the samples treated with thymol at 10% and at 30% (FIG. 9 curves B and C respectively), show the presence of diffraction peaks at about 2θ equal to 9.8°, 16.1°, 19.9°, indicating the presence of a co-crystalline phase.

Figure 10:
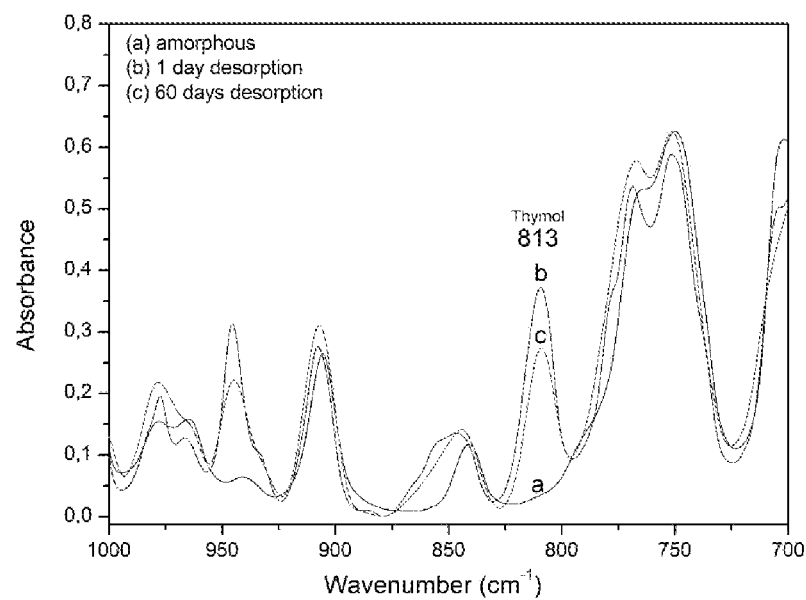
FIG. 10 shows the FTIR spectra of the amorphous syndiotactic polystyrene flock obtained as described in Example 1 (curve a) and of the corresponding flock activated with thymol in a methyl-acetate solution at 30% by weight as described in example 3e after 1 day (curve b) or 60 days (curve c) of desorption in air.
Figure 11:
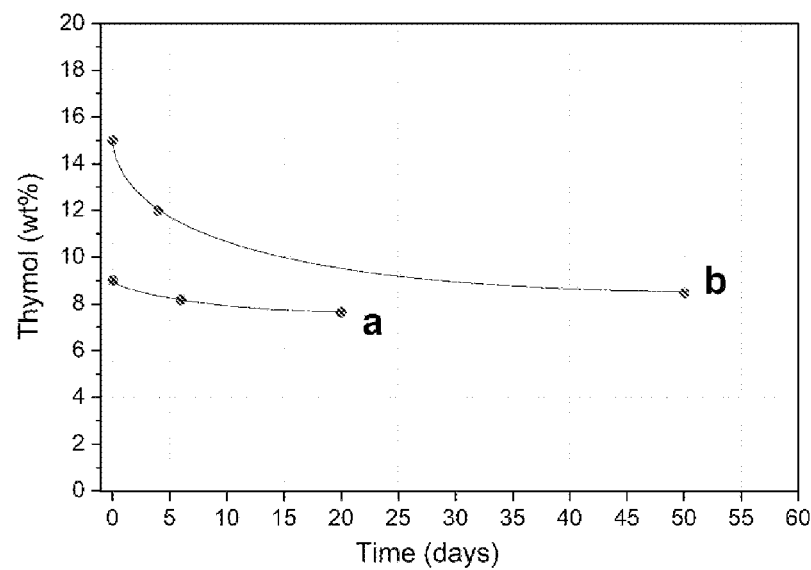
FIG. 11 shows the desorption kinetics in air of thymol from the flock activated with thymol in a methyl-acetate solution at 10% by weight (curve a) and from the flock activated with thymol in a methyl-acetate solution at 30% by weight (curve b), obtained as described in example 3e.

FTIR spectra, using DRIFT technology of the amorphous flock and of the flock activated using the 30% methylacetate solution of thymol were compared in FIG. 10 (curves b and c). The presence of peaks typical of the helix shape of s-PS (for example, the peak at 571 cm$^{-1}$ in an area of the spectrum not shown in FIG. 10) and the presence of absorption peaks of thymol (for example, the peak at 813 cm$^{-1}$) clearly confirm the formation of the syndiotactic polystyrene/thymol co-crystalline phase. Kinetics for the desorption of thymol by the two samples are shown in FIG. 11.

After 30 days from the preparation, the flock activated with the 30% methyl-acetate solution of thymol was subjected to a thermogravimetric analysis and a concentration of thymol equal to 10% by weight was observed.

An anti-microbial assay according to the UNI EN ISO 20743 method was then conducted on the flock to evaluate the anti-microbial effectiveness with respect to the *Staphylococcus aureus* strain.

Figure 12:
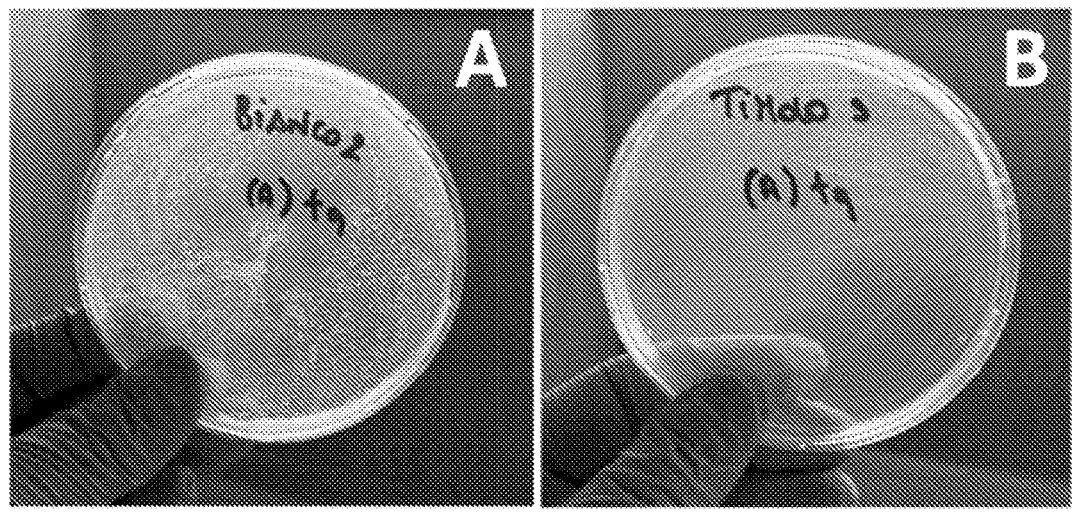
FIG. 12 is a photographic image showing the results of the anti-microbial assay, which shows the bacterial growth in a Petri dish containing medium treated with the flock obtained in Example 1 (panel A) or the flock activated with thymol in a methyl-acetate solution at 30% by weight (panel B), as described in Example 3e.

As shown in FIG. 12, no bacterial growth was observed in the Petri dishes treated with the activated flock. Thus, this experiment shows that the flock is capable of releasing eugenol in water at amounts suitable to obtain an antibacterial effect, i.e. so as to exceed the Minimum Inhibitory Concentration (MIC=0.662 mg/mL).

Example 4—Preparing the Textile

Example 4a

The activated syndiotactic polystyrene flock of example 3d containing 20% of eugenol was used for obtaining—by cotton spinning an intimate blend yarn, with metric number Nm equal to 40 (40 km of filament per one kg), containing 96% of cotton and 4% of activate syndiotactic polystyrene. A cone of such yarn is shown in FIG. 13A.

Figure 13:
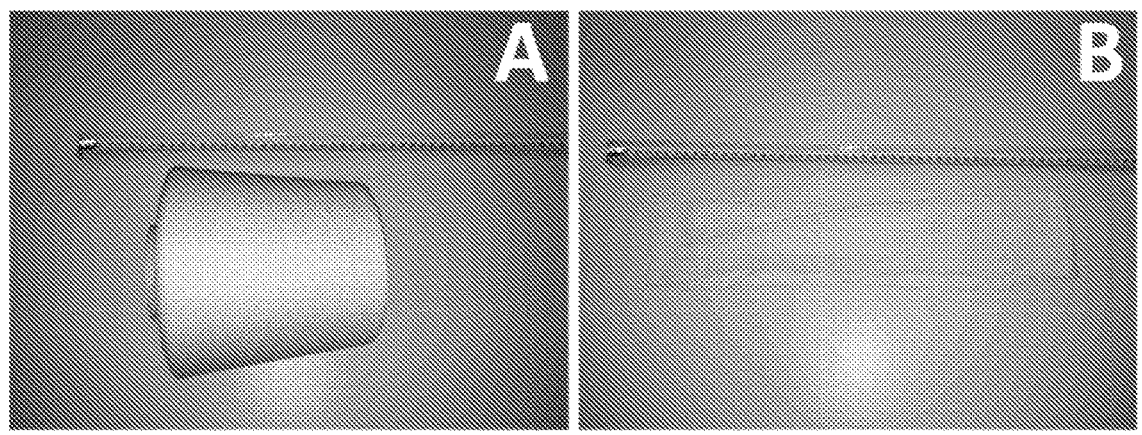

Such activated yarn was used for making, using a circular knitting machine, a stockinette stitch textile, shown in FIG. 13B.

The obtained yarn has an initial content of eugenol equal to about 0.8%. After one year at ambient temperature, the eugenol content of the yarn is close to 0.1%.

Example 4b

Figure 14:
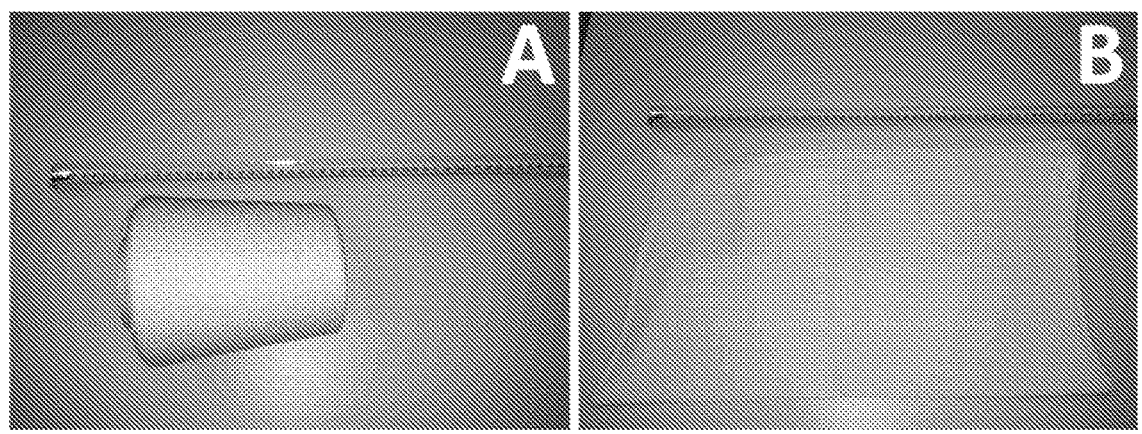
FIG. 14 is a photographic image showing a cone yarn (panel A) and a textile (panel B) containing 30% of syndiotactic polystyrene and 70% of cotton, obtained as described in Example 4b.

The syndiotactic polystyrene filament with metric number Nm equal to 34 was used as a core of a yarn with metric number Nm equal to 12, which was covered using a cotton fibre, by means of cotton spinning. The obtained core yarn contains 70% of cotton and 30% of syndiotactic polystyrene and it is shown in FIG. 14A. Such yarn was used for making, using a straight knitting machine, a stockinette stitch textile, shown in FIG. 14B.

Example 5—Regenerating the Active Flock

Example 5a

The activated syndiotactic polystyrene flock of example 3d—which upon activation (by the aqueous emulsion with a eugenol content equal to 0.6% by weight) had an eugenol content equal to 30% by weight, after one year at ambient temperature and in air has a eugenol content reduced at about 10% by weight.

The amount of eugenol in the flock is restored using an alcoholic solution containing eugenol. In particular, the flock is immerged for 30 minutes in an ethanol solution with a eugenol content equal to about 10% by weight.

An increase of eugenol content in the flock from 10% to about 20% by weight was observed.

Example 5b

The activated syndiotactic polystyrene flock of example 3d—which upon activation (by the aqueous emulsion with a eugenol content equal to 0.6% by weight) had absorbed 30% by weight of eugenol,—after one year at ambient temperature and in air has a eugenol content reduced at about 10% by weight.

The amount of eugenol in the flock is restored using an aqueous solution containing eugenol. In particular, the flock is immerged for 30 minutes in an aqueous solution with a eugenol content equal to about 0.2% or in an aqueous emulsion with a eugenol content equal to 0.3% by weight.

An increase of eugenol content in the flock from 10% to about 15% and to about 25% by weight, respectively, was observed.

Example 5c

After more than one year from preparation, a syndiotactic polystyrene flock activated according to the method of example 3d has a eugenol content equal to 5% by weight.

The flock is washed for 30 minutes in an aqueous cleaning solution, which includes 15% by weight of sodium lauryl phosphate, rinsed for 5 minutes in an aqueous emulsion with a eugenol concentration equal to 0.3%, and dried in a dryer at 60° C. for 10 mins.

The presence of eugenol content equal to 10% by weight was observed.

The invention claimed is:

1. Yarn comprising at least 1% by weight of fibres of a syndiotactic polystyrene containing a co-crystalline phase comprising at least one active guest compound and characterised by a X-ray diffraction (CuKα) pattern comprising peaks having maxima at about 2θ: between 9.5° and 9.8°, between 16.3° and 16.6°, between 19.7° and 20°.

2. Yarn according to claim 1 wherein said active compound has anti-microbial, pharmacological, or cosmetic activity.

3. Yarn according to claim 1, wherein said active compound has a molecular volume smaller than 0.4 nm³.

4. Yarn according to claim 1, wherein said active compound also has an acid dissociation constant pKa>8, basic dissociation constant pKb>8, relative dielectric constant <20 and absence of solvent capacity with respect to syndiotactic polystyrene at temperatures below 100° C.

5. Yarn according to claim 1, wherein said active compound is contained in the syndiotactic polymer in an amount greater than 1% by weight, with respect to the total weight of the polymer and/or active guest compound is contained in the syndiotactic polymer in an amount comprised between 5 and 50%.

6. Yarn according to claim 1, comprising fibres of said syndiotactic polystyrene at an amount comprised between 1 and 100% by weight, with respect to the total weight of the yarn and natural and/or synthetic textile fibres at an amount between 0 and 99% by weight, with respect to the total weight of the yarn.

7. Yarn according to claim 1, comprising fibres of said syndiotactic polystyrene and one or more natural and/or synthetic textile fibres.

8. Yarn according to claim 1, whose fibres consist in fibres of said syndiotactic polystyrene.

9. A textile comprising a yarn according to claim 1 and wherein said fibres of syndiotactic polystyrene constitute at least 1% by weight of the textile.

10. Yarn according to claim 1 wherein said active compound is selected from the group consisting of acetylsalicylic acid, isoniazid, methazolamide, metronidazole, sulfacetamide, butylated hydroxyanisole, decanoic acid, butyl acetate, diacetyl, diallyl disulfide, ethyl acetate, guaiacol, linalool, anethole, camphor, carvacrol, carvone, coumarin, eugenol, hexanal, tyrosol, geraniol, isoprenol, limonene, menthol, myrcene, caffeic acid, cinnamic acid, catechol, pyrogallol, thymol, and mixtures thereof.

11. Yarn according to claim 1, wherein said active compound is contained in the syndiotactic polymer in an amount greater than 5% by weight, with respect to the total weight of the polymer and/or active guest compound is contained in the syndiotactic polymer in an amount comprised between 10 and 30%.

12. Yarn according to claim 1, comprising fibres of said syndiotactic polystyrene at an amount comprised between 5 and 100% by weight, with respect to the total weight of the yarn and natural and/or synthetic textile fibres at an amount between 0 and 95% by weight, with respect to the total weight of the yarn.

13. Yarn according to claim 1, comprising fibres of said syndiotactic polystyrene at an amount comprised between 20 and 100% by weight, with respect to the total weight of the yarn and natural and/or synthetic textile fibres at an amount between 0 and 80% by weight, with respect to the total weight of the yarn.

* * * * *